United States Patent [19]

Verde-Casanova et al.

[11] Patent Number: 5,834,490

[45] Date of Patent: Nov. 10, 1998

[54] CYCLOPROPYL DERIVATIVES, PREPARATION METHOD THERE-OF AND APPLICATIONS

[75] Inventors: María José Verde-Casanova; Alvaro Galiano-Ramos, both of Madrid, Spain

[73] Assignee: Instituto de Investigacion y Desarrolo Quimico Biologico, S.A., Al cobendas, Spain

[21] Appl. No.: 912,250

[22] Filed: Aug. 15, 1997

Related U.S. Application Data

[63] Continuation of Ser. No. 481,276, Dec. 6, 1995, abandoned.

[30] Foreign Application Priority Data

Nov. 4, 1993 [ES] Spain ....................................... 9302303

[51] Int. Cl.$^6$ ........................ A61K 31/445; C07D 211/34
[52] U.S. Cl. ........................... 514/330; 546/225; 546/227
[58] Field of Search ........................... 514/330; 546/225, 546/227

[56] References Cited

FOREIGN PATENT DOCUMENTS

| | | |
|---|---|---|
| 239710 | 10/1987 | European Pat. Off. . |
| 460315 | 4/1978 | Spain . |
| 889225 | 2/1952 | United Kingdom . |
| 775749 | 5/1957 | United Kingdom . |
| 869978 | 6/1961 | United Kingdom . |

OTHER PUBLICATIONS

1958 Chem. Abst. 52: #14609e.
1982 Chem. Abst. 97: 190 174482b.
Blaney et al. (1983) J. Medicin. Chem. 26:1747–52.
Ekenstam et al. (1958) Org. Chem. 10:14609.
Feldman et al. (1988) Anesth. Analg 67:1047–52.
Local Anesthetics (1987) G.R. Strickark ed., p. 191.
The Merck Index (1996) XII ed., p. 8418 (Record #8417).

Primary Examiner—Ceila Chang
Attorney, Agent, or Firm—Klauber & Jackson

[57] ABSTRACT

Cyclopropyl derivatives of formula (I) wherein R is cyclopropyl or methylcyclopropyl are prepared by reaction of 2,6-dibromohexanoyl chloride with 2,6-dimethylaniline in the presence of a base at 0°–25° C. to give 2,6-dibromohexanoyl-2,6-dimethylanilide which subsequently is reacted with R—NH$_2$ (wherein R is cyclopropyl or methylcyclopropyl) at 70°–100° C. The compounds are useful as antiarrhythmic agents and as local anaesthetic agents.

6 Claims, 2 Drawing Sheets

CYCLOPROPYL DERIVATIVES, PREPARATION METHOD THERE-OF AND APPLICATIONS

RELATED APPLICATIONS

This application is a continuation of U.S. Ser. No. 08/481,276, filed Dec. 6, 1995, now abandoned, which is a national phase entry of PCT/ES94/00107, filed Nov. 3, 1994.

TECHNICAL FIELD OF THE INVENTION

The present invention fits in the technical field of obtainment of products with antiarrythmic and local anaesthetic activity.

More specifically, the present invention provides new cyclopropyl derivatives and a preparation method that have excellent antiarrythmic and local anaesthetic activity.

PRIOR ART OF THE INVENTION

The group of sodium channel inhibitors is characterized in its common activity as antiarrythmic and local anaesthetic agents. From the point of view of the latter, all of them produce a reduction of sensorial conduction of the nerve impulses close to where they are administered. This activity is reversible and the effects disappear in a few minutes.

The use of local anaesthetic agents has increased in the last few years due to their use in certain types of anaesthesia such as spinal anaesthesia, brachial anaesthesia, etc., together with the increase of surgery on out-patients and new less bloody surgical techniques designed to reduce hospital costs.

The therapeutic family of local anaesthesias is characterized on the one hand in its extensive use in different areas of surgery and, in its large number of molecules described with local anaesthetic activity. Despite the large number of molecules described, doctors can only choose a few as there are no more than 3 or 4 compounds that are presently available on the market. Among these, the ones used the most are mepivacain and bupivacain that provide excellent results in most patients. However, side effects are observed in 5–10% of the cases particularly in patients when adrenaline is added to the formulations for the purpose of increasing the duration of anaesthesia.

In effect, most local anaesthetics that are known are very rapidly metabolized and, besides, they increase the blood flow that takes place in the area of the injection that obliges a vasoconstrictor to be included in the formulations. Hence, it can be concluded that it would be desirable to eliminate the cardiac risk that the use of adrenaline involves maintaining the characteristics of duration of the effect.

The authors of the present invention have reached the conclusion that introducing a cyclopropyl group in the general structure of local anaesthetics of the family of mepivacain and bupivacain has a beneficial effect on the activity and duration of the effect. The cyclopropyl group is characterized, in effect, in that it has lipophilic properties similar to those of the corresponding linear alky groups, improving at the same time the resistance to metabolization and the properties of distribution in the organic liquids.

Consequently, the present invention provides new products that contain the cyclopropyl group and that have local anaesthetic and antiarrythmic properties that are characterized in a long duration of the effect without the need to resort to the use of vasoconstrictors.

DETAILED DESCRIPTION OF THE INVENTION

As indicated in the title, the present invention refers to new cyclopropyl derivatives, a preparation method thereof and application thereof as antiarrythmic agents and as local anaesthetics.

The new cyclopropyl derivatives of the present invention are characterized in that they have the following general formula (I):

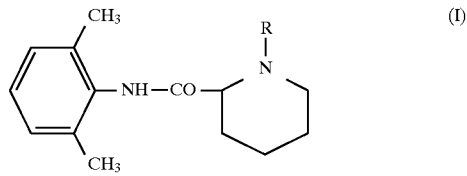

wherein R represents a cyclopropy or methylcyclopropyl, said formula (I) including the racemic mixtures as well as the enantiomers or optical isomers separately, as well as pharmaceutically acceptable acid addition salts thereof, especially hydrochloride.

The compounds of formula (I), that can be named chemically as N(-cyclopropyl or methylcyclopropyl-piperidin-2-carboxylanilides) are obtained by the following process: reacting 2,6-dibromohexanoyl with 2,6-dimethylaniline in a suitable solvent and in the presence of a second base equivalent, at a temperature between 0° and 25° C., to give 2,6-dibromohexanoyl-2,6-dimethylanilide, that is reacted with cyclopropyl or methylcyclopropyl cycling to cyclopropyl or N-methylcyclopropyl, dl, piperidin-2-carboxyl-2,6-dimethylanilide.

This compound can be transformed into the corresponding pharmaceutically acceptable acid addition salt by means of the normal processes. Thus, for example, the corresponding hydrochloride is obtained by reacting with dry hydrochloric acid in acetone.

The base used in the reaction of 2,6-dibromohexanoyl chloride with 2,6-dimethylaniline can be any suitable base that does not undesirably interfere in the course of the reaction. In particular, trimethylamine and pyridine can be mentioned. The solvent used in said reaction has to be an aprotic solvent.

The reaction of 2,6-dibromohexanoyl-2,6-dimethylanilide with cyclopropyl or methylcyclopropylamine (that can be represented by the general formula R—NH$_2$ wherein R has the meaning given above) can be carried out either with an excess of R—NH$_3$ (3 equivalents) per equivalent of anilide, or else by using a single equivalent of R—NH$_2$ and two other equivalents of another suitable base similar to the one indicated above for the first part of the process. Besides, this reaction is also carried out in an aprotic solvent and at a temperature between 70° and 100° C. approximately. The cited aprotic solvent may be dioxane, acetonitrile or a similar solvent.

The products of both steps of the process are easily isolated by eliminating the solvent and agitating with water to dissolve the salts formed, after which they are filtered and purified in the normal way, normally recrystallization in the solvent or suitable one.

The enantiomers or optical isomers separately can be obtained either by carrying out the process described above in a stereoselective manner, or else by separating the optical isomers from the racemic mixture by conventional methods such as fractioned crystallization, chromatography, etc.

EMBODIMENTS OF THE INVENTION

Figure 1:
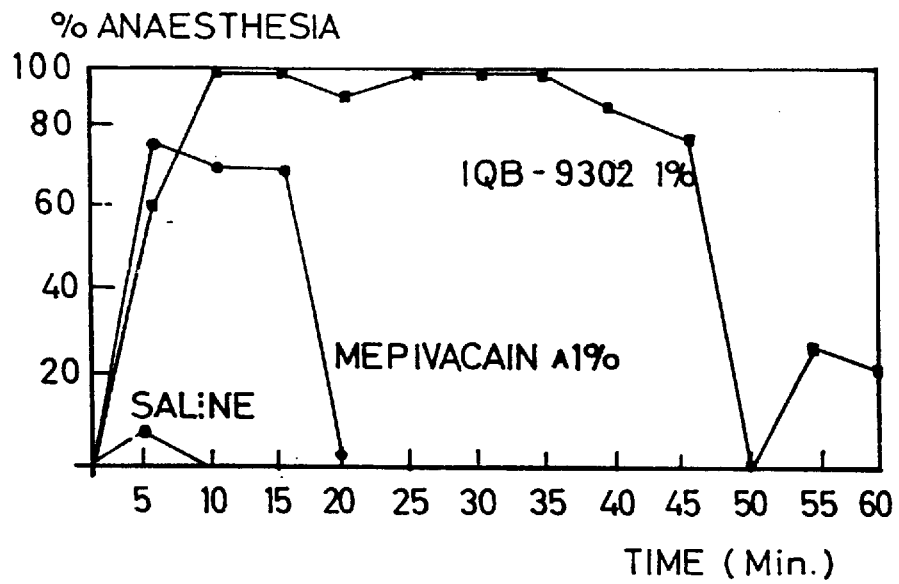
FIG. 1 is a graph of the superficial anaesthetic activity of the product IQB-9302 of the invention in comparison with mepivacain.

The following examples describe in full detail the invention, without those details that do not change the essence of the same constituting a limiting factor.

EXAMPLE I

Preparation of dl,N-cyclopropyl-piperidin-2-carboxyl-2,6-dimethylanilide hydrochloride (IQB-9301)

A) Preparation of 2,6-dibromohexanoyl-2,6-dimethylanilide

A mixture of 4.04 g. (0.04 mol) of triethylamine and 4.84 g. (0.04 mol) of 2,6-dimethylaniline in 10 ml. of dichloromethane is added drop by drop to 11.3 g. (0.40 mol) of 2,6-dibromohexanoyl chloride dissolved in 50 ml. of dichloromethane with agitation and cooling in an ice bath. The reaction mixture is agitated at room temperature for 30 minutes.

The solvent is vacuum eliminated and the residue is agitated with water. The white solid formed is filtered and washed with ethanol and ether. The ethanol is recrystallized. 10.5 g. are obtained.

Yield: 70% m.p.: 99°–100° C.

H-NMR: ($Cl_3CD$) 300 MHz δ in ppm 7.71 (s, 1H); 7.25–7.05 (m,3H), 4.5 (m,1H); 3.43 (t,2H), 2.23 (s,6H); 2.40–1.50 (m,6H)

B) Preparation of dl,N-cyclopropyl-piperidin-2-carboxyl-2,6-dimethylanilide 4.04 g. (0.04 mol) of triethylamine and 1.19 g. (0.021 mol) of cyclopropylamine are added to a solution of 7.54 g. (0.02 mol) of 2,6-dibromohexanoyl-2,6-dimetylanilide in 100 ml. of dioxane. The reaction mixture is gently refluxed for 10 h. Then it is left to cool and the white solid of triethylamine bromohydrate formed is filtered.

The filtrate is vacuum evaporated and the residue is agitated with water and filtered. The solid obtained is dissolved in 50 ml. of 0.1N HCl and extracted with dichloromethane. The acid solution is neutralized with NaOH and the solid is filtered.

It is purified by washing with hot n-hexane and passing it through silica gel with a mixture of dichloro-methane-acetone (95:5) as an eluent. 4 g of white solid are obtained.

Yield: 73% m.p.: 175°–176° C.

$^1$H-NMR: ($Cl_3CD$) 300 MHz δ in ppm 8.54 (s,1H); 7.06 (m,3H); 3.56 (m,1H); 3.09–2.84 (m,2H), 2.48 (m,1H); 2.22 (s,6H), 1.89–1.35 (m,6H); 0.62–0.44 (m,4H)

C) Preparation of dl,N-cyclopropyl-piperidin-2-carboxyl-2,6-dimethylanilide hydrochloride (IQB-9301)

3.5 g of the base obtained in the previous step are dissolved in 50 ml. of acetone. A dry hydrochloric acid steam is passed through it. The hydrochloride formed is filtered and washed with acetone. Absolute ethanol recrystallization. 3.2 g. are obtained.

Yield: 80% m.p.: 249°–250° C.

$^1$H-NMR: (DMSO-$d_6$) 300 MHz δ in ppm 10.46 (s,1H), 9.54 (s,1H); 7.06 (m,3H); 4.39 (m,1H); 3.26 (m,2H), 2.89 (m,1H); 2.16 (m,6H), 1.95–0.77 (m,10H)

EXAMPLE 2

Preparation of dl,N-methylcyclopropyl-piperidin-2-carboxyl-2,6-dimethylanilide hydrochloride (IQB-9302)

It was prepared in the same conditions described in example 1 part B), from 7.54 g (0.02 mol) of 2,6-dibromohexanolyl-2,6-dimethylanilide and from 1.42 g (0.02 mol) of methylcycloproylamine and 4.04 g (0.04 mol) of triethylamine. 4.4 g are obtained.

Yield: 77% m.p.: 123°–124° C.

$^1$H-NMR: (DMSO-$d_6$) δ in ppm 8.20 (s,1H), 7.05 (m,3H); 3.43 (2t,1H), 2.95 (m,2H); 2.24 (d,6H); 2.09 (m,2H); 1.99–1.31 (m,6H); 0.89 (m,1H), 0.57 (dd,2H), 0.15 (dd,2H)

B) Preparation of dl,N-methylcyclopropyl-piperidin-2-carboxyl-2,6-dimethylanilide hydrochloride (IQB-9302)

A dry hydrochloric acid stream was passed through 2.5 g. of the base prepared in the above section and dissolved in acetone.

Ethanol recrystallization. 2.2 g are obtained.

Yield: 80% m.p.: 264°–265° C.

$^1$H-NMR: (DMSO-$d_6$) δ in ppm 10.62 (s,1H); 9.84 (s,1H), 7.08 (m,3H), 4.27 (m,1H); 3.10 (m,2H), 2.89 (m,2H), 2.14 (m,1H); 2.06 (m,6H); 1.90–1.00 (m,6H); 0.68 (t,2H); 0.36 (t,2H)

COMPARATIVE EXAMPLE OF THE LOCAL ANAESTHETIC ACTIVITY OF THE COMPOUNDS OF THE INVENTION

Superficial anaesthesia in rabbits:

The local anaesthetic effects of the compounds of the invention were compared with commercial mepivacain according to the Rose method (1931) of palpebral reflex inhibition. Under normal conditions, stimulation of the cornea of a rabbit's eye by means of a hair causes the eyelids to close. If the cornea has been previously subjected to the action of a local anaesthetic, the reflex is not produced with a single stimulation; in order to cause it, the stimulation must be repeated a certain number of times and if the anaesthesia is deep, it is seen that the cornea is practically insensible.

The following concentrations of the following drugs were used in these studies:

Mepivacain 1%

IQB-9301 1%

IQB-9302 1% which were instilled in a volume of 0.1 ml. in one of the eyes of a series of albino rabbits from New Zealand. Stimuation started two minutes after the drug was administered and continued until the total recovery of the palpebral reflex.

For each one of the drugs between 5 and 7 animals were used.

Anaesthesia by infiltration:

Albino Guinea pigs of both sexes with a body weight of 400 to 600 g. whose hair was removed the day before the experiment were used. The drugs used (mepivacain, IQB-9301 and IQB-9302) were injected intradermally in 4 spots of the dorsal region, in a volume of 0.2 ml., using the same volume of saline solution as a control. The anaesthetic action was evaluated by making note of the responses (all or nothing) to the stimulus (6 pricks in each one of the spots) produced at 5 minute intervals for 30 minutes.

The drugs used were the following:

Mepivacain 1%

IQB-9301 1%

IQB-9302 1%

IQB-9302 0.5%

IQB-9302 0.1%

For each one of these concentrations a group of 8 animals was used.

RESULTS

Figure 2:
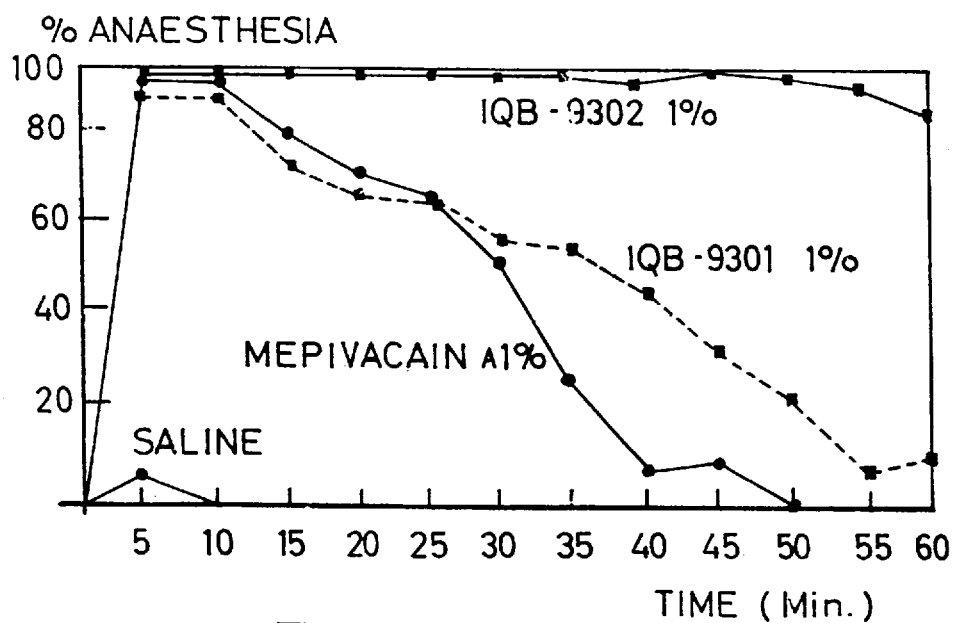
FIG. 2 is a graph of the intradermal local anaesthetic activity of the compounds IQB-9301 and IQB-9302 of the invention in comparison with mepivacain.
Figure 3:
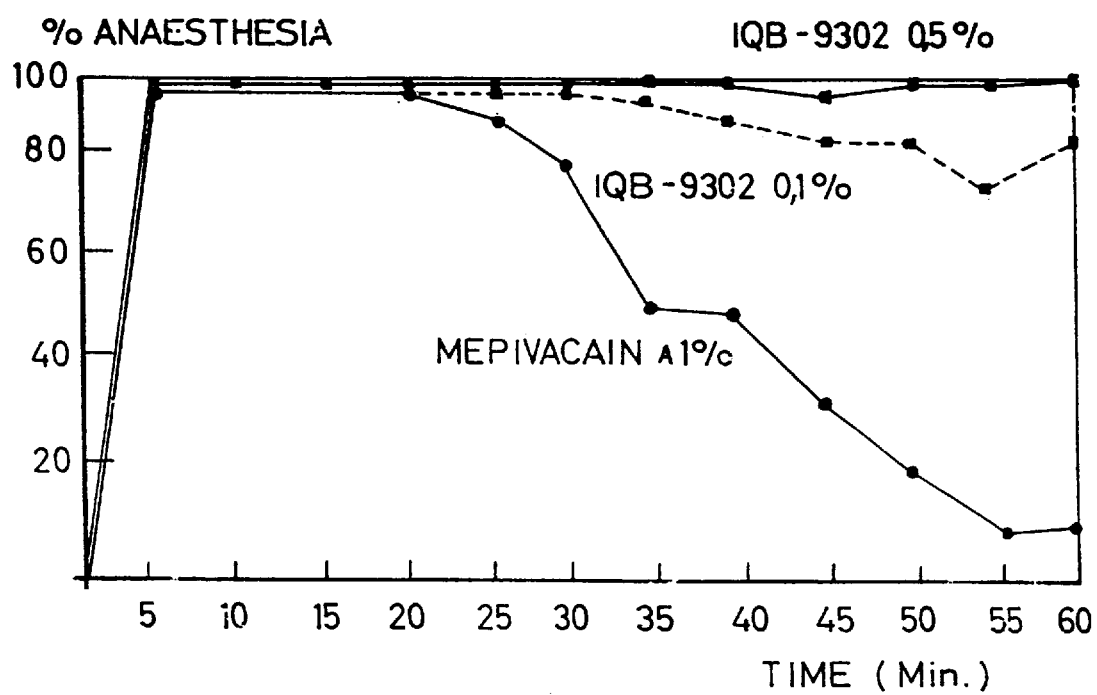
FIG. 3 is another graph of the intradermal local anaesthic activity of the compounds of the invention IQB-9301 and IQB-9302 in comparison with mepivacain, at different concentrations from those used for FIG. 2.

FIGS. 1, 2 and 3 summarize the results obtained with the products of the invention in comparison with mepivacain, one of the local anaesthetics prescribed the most.

Mepivacain 1% was effective in the rabbit's eye inhibiting only 80% of the stimuli. Besides, the effect was rather transitory, disappearing after 10 minutes. IQB-9301 was practically ineffective in this test. On the contrary, IQB-9302 reached 100% effectiveness maintaining a strong anaesthetic effect for more than 45 minutes.

FIG. 2 shows that IQB-9301 and mepivacain 1% were equally effective in anaesthesia by infiltration. In both cases practically 100% effectiveness was reached for 10 to 15 minutes. IQB-9302 was much more effective than the other two products at the same concentration: after 60 minutes, the anaesthetic effect was still 100%.

FIG. 3 shows the comparative effects of mepivacain 1% with IQB-9302 0.5 and 0.1%. Both concentrations of IQB-9302 were more effective than mepivacain, maintaining a 100% effect after 60 minutes at a concentration of 0.5%.

These results allow one to reach the following conclusions:

The two products of the invention act as strong local anaesthetics being equivalent or stronger than mepivacain.

The beginning of the action is practically the same for the three products.

IQB-9302 is between 5 and 15 times stronger than mepivacain, since concentrations 10 times weaker produce a greater effect.

The duration of the effect of IQB-9302 is also longer than that of mepivacain (2 to 5 times.)

We claim:

1. A compound of the following formula (I):

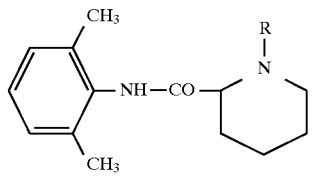

wherein R is cyclopropyl or methylcyclopropyl, said formula (I) including the racemic mixtures as well as the enantiomers or optical isomers separately, as well as the pharmaceutically acceptable acid addition salts.

2. A compound according to claim selected from the group consisting of:

dl,N-cyclopropyl-piperidin-2-carboxyl-2,6-dimethylanilide, or its optical isomers (d) and (l);

dl,N-cyclopropyl-piperidin-2-carboxyl-2,6-dimethylanilide hydrochloride, or its optical isomers (d) and (l);

dl,N-methylcyclopropyl-piperidin-2-carboxyl-2,6-dimethylanilide, or its optical isomers (d) and (l)

dl,N-methylcyclopropyl-piperidin-2-carboxyl-2,6-dimethylanilide hydrochloride, or its optical isomers (d) and (l).

3. A process for the preparation of cyclopropyl compound of formula (I):

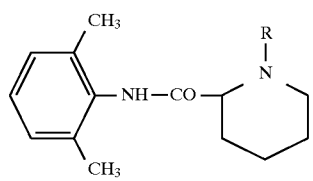

wherein R is cyclopropyl or methylcyclopropyl; whose process is characterized in that it comprises reacting 2,6-dibromohexanoyl chloride with 2,6-dimethylaniline in a suitable solvent and in the presence of a second base equivalent, at a temperature between 0° and 25° C., to give 2,6-dibromohexanoyl-2,6-dimethylanilide, that is reacted with cyclopropyl or methylcyclopropylamine cycling to N-cyclopropyl or N-methylcyclopropyl, dl, piperidin-2-carboxyl-2,6-dimethylanilide, in a suitable solvent and at a temperature between 70° and 100° C.; and optionally transforming the product thus obtained into a pharmaceutically acceptable acid addition salt; and/or separating the racemic mixture into its enantiomers or optical isomers, which can also be obtained, by carrying out the process under sterospecific conditions.

4. A process according to claim 3, characterized in that the compound of formula (I) is selected from the group consisting of:

dl,N-cyclopropyl-piperidin-2-carboxyl-2,6-dimethylanilide, or its optical isomers (d) or (l);

dl,N-cyclopropyl-piperidin-2-carboxyl-2,6-dimethylanilide hydrochloride, or its optical isomers (d) or (l);

dl,N-methylcyclopropyl-piperidin-2-carboxyl-2,6-dimethylanilide, or its optical isomers (d) or (l);

dl,N-methylcyclopropyl-piperidin-2-carboxyl-2,6-dimethylanilide hydrochloride, or its optical isomers (d) or (l).

5. A method of treating arrythmia or inducing local anaesthesia comprising administration of a compound of formula (I):

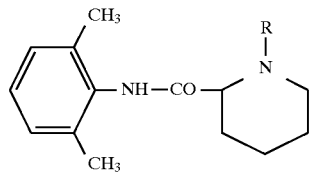

wherein R is cyclopropyl or methylcyclopropyl, said formula (I) including the racemic mixtures as well as the enantiomers or optical isomers separately as well as the pharmaceutically acceptable acid addition salts to a patient in need of such therapy.

6. A method according to claim 5, characterized in that the compound of formula (I) is selected from the group consisting of:

dl,N-cyclopropyl-piperidin-2-carboxyl-2,6-dimethylanilide or its optical isomers (d) or (l);

dl,N-cyclopropyl-piperidin-2-carboxyl-2,6-dimethylanilide hydrochloride or its optical isomers (d) or (l);

dl,N-methylcyclopropyl-piperidin-2-carboxyl-2,6-dimethylanilide or its optical isomers (d) or (l);

dl,N-methylcyclopropyl-piperidin-2-carboxyl-2,6-dimethylanilide hydrochloride or its optical isomers (d) or (l).

* * * * *